United States Patent [19]

Kopp et al.

[11] 4,289,750

[45] Sep. 15, 1981

[54] THERAPY OF CONDITIONS WHICH MAY BE ASSOCIATED WITH ALTERED RENAL FUNCTION AND DOSAGE FORMS THEREFOR

[76] Inventors: Klaus F. Kopp, Aschlkofener Str. 4, D-8017 Ebersberg; Joachim W. Helbig, Traubinger Str. 23, D-8132 Tutzing, both of Fed. Rep. of Germany

[21] Appl. No.: 85,066

[22] Filed: Oct. 15, 1979

[30] Foreign Application Priority Data

Oct. 16, 1978 [DE] Fed. Rep. of Germany ....... 2845059

[51] Int. Cl.$^3$ .................... A61K 33/00; A61K 33/06; A61K 33/14
[52] U.S. Cl. ........................................ 424/33; 424/35; 424/81; 424/127; 424/153; 424/154; 424/317; 424/322
[58] Field of Search ................. 424/127, 81, 153, 154, 424/33, 35, 317, 322

[56] References Cited

U.S. PATENT DOCUMENTS

| | | | |
|---|---|---|---|
| 3,081,233 | 3/1963 | Enz et al. ............................. | 424/33 |
| 3,960,757 | 6/1976 | Morishita et al. ................ | 424/35 X |
| 3,968,277 | 7/1976 | Takase ............................. | 424/81 X |

FOREIGN PATENT DOCUMENTS 287292  4/1914  Fed. Rep. of Germany .

OTHER PUBLICATIONS

Husted, F. et al., *J. Clin. Invest.*, 56, 414–419 (1975).
Richards, P. et al., *The Lancet*, 1972 (vol. 2), 994–997.
Bishop, M. et al., *Brit. Med. J.*, 4, 529 (1972).
Pak, Z. et al., *Voen Med Zh*, 0(9): 78–79 (1974), Listed in Cumulated Index Medicus, Subject Index, p. 803 (1975).
Barmatskii, V. et al., Klin. Med., 56(7), 66–70 (1978), Listed in Cumulated Index Medicus, Subject Index, p. 5469 (1978).
*Chemical Abstracts*, 77: 168614s (1972) [OLS No. 2,209,244, 9/21/72].
Strauss, M. et al. (Editors), *Diseases of the Kidney*, vol. 1, Second Edition, Little Brown, Boston, pp. 244–245.
Bleich, H., *Metabolic Acidosis*, American Physiological Society, 1976, Preface, pp. 17 and 19.
Kopp, K., Reprint of Lecture Delivered in Murnav, Germany, 9/25/76: Diagnosis and Therapy of Kidney Function Disturbances in the Seriously Injured.
Merck Index, Seventh Edition, Merck and Co., Inc., Rahway, N.J., 1960, p. 946.
Pitts, R., Physiology of the Kidney and Body Fluids, 3rd Ed., Yearbook Medical Publishers, Inc., Chicago, 1971, pp. 198–200.
*Arzneimittelbrief*, 12(6), pp. 61–64 (1978).
Garella, S. et al., *Kidney International*, 8, 279–283 (1975).
Kanter, G., *Canadian J. Biochem. Phys.*, 41, 1399–1407 (1963).
McSherry, E., *Kidney International*, 14, 349–354 (1978).

*Primary Examiner*—Richard A. Schwartz
*Attorney, Agent, or Firm*—Browdy and Neimark

[57] ABSTRACT

The invention concerns a method of treating a subject suffering from abnormal distribution and retention of body fluids such as may be the result of altered renal function, which comprises the step of administering to a subject in need of such treatment, a therapeutically effective amount of a pharmaceutically acceptable alkaline acting substance capable of increasing patient plasma bicarbonate level to a value in excess of that prior to treatment.

Oral preparations, in particular an alkaline substance capable of releasing bicarbonate ions, for therapy of a large variety of ailments and diseases, are disclosed.

22 Claims, No Drawings

THERAPY OF CONDITIONS WHICH MAY BE ASSOCIATED WITH ALTERED RENAL FUNCTION AND DOSAGE FORMS THEREFOR

This invention relates to novel procedures for treating patients suffering from abnormal distribution and retention of body fluids such as may be the result of altered renal function. Accompanied by corrections of body fluid distributions, such as may be achieved by an increased renal function of a patient suffering from the effects of altered renal function, increased passage of retention products normally entrained in the urine can also be achieved. Furthermore, the invention provides for prophylactic treatment of patients liable to contract renal failure. The invention also provides for prophylactic treatment and treatment of patients having or being inclined to form kidney stones. In general, the common feature of the variety of ailments treated or the corrective measures taken are associated with altered renal function or renal insufficiency. Particularly, the invention can involve some procedures attempted in the past which have not comprised recognition of the patient condition which should be established in accordance with the treatment procedures of the present invention. Considered to be of particular importance are pharmaceutical preparations of the present invention suitable for treating a variety of ailments associated with altered renal function.

Physiological studies have shown that a deficit of sodium bicarbonate in the blood and extracellular fluid can lead to a condition described as "acidotic volume expansion".

Another physiological phenomen is that the healthy kidney generates and retains more bicarbonate in the body when a deficiency of fluid in the blood and extracellular volume arises. In this fashion, a healthy patient subjected to body fluid volume contraction will enter into a state of moderate alkalosis.

The above physiological phenomena have not in the past been recognised as providing a potential for therapeutic treatment of ailments and illnesses associated with altered kidney function. Thus, although there have been suggestions in the past to attempt neutralising chronic states of metabolic acidosis, for example by intravenous injection of sodium bicarbonate solution, such procedures have in general been considered to involve some danger to the patient, particularly when the patient is suffering from high blood pressure such as is frequently the case. Similarly, the generally recognised teachings suggest that hypersodemia can develop following on such administration which can lead to such consequences as high blood pressure, cardiac insufficiency, and pulmonary and peripheral edema. Overall, there is a strong prejudice against administration of sodium bicarbonate in the treatment of ailments associated with altered renal function. What is not generally known however is that complications such as have been experienced and described, are in fact not as a direct result of the presence of sodium bicarbonate itself, but rather of secondary changes in sodium, potassium, and calcium levels. This could not easily be recognised in view of the lack of availability of suitable laboratory methods.

At the onset of acute renal failure, a sudden increase in the rate of generation of predominantly non-volatile organic acids takes place which results in a rapid consumption of extracellular bicarbonate buffer reserves. There is now believed to be sufficient evidence available to conclude that oligoanuria, as may arise from early or late complications following on severe medical, surgical or traumatic conditions, is closely linked to this rapid consumption of bicarbonate buffer reserve and the inability of the failing kidney to eliminate accumulating hydrogen ion excess. These considerations have been overlooked or neglected in therapy in the past. One reason is probably that moderate renal acidosis has in the past incorrectly been considered to be harmless.

Attempt to neutralise, even in part, metabolic acidosis for example by administration of sodium bicarbonate has in general been avoided for reasons such as already mentioned and more particularly since bicarbonate loading of a patient has incorrectly been considered to depress renal function.

In contrast to practically all indications of the past, it has been found in accordance with the invention that administration of an alkaline acting substance, in particular one which liberates sodium and bicarbonate ions, in sufficient amount to raise patient plasma bicarbonate level, can in a large number of cases be highly effectively employed in the therapeutic or prophylactic treatment of a large variety of ailments involving abnormal distribution and retention of body fluids such as may be the result of altered renal function, or renal failure as may arise under circumstances such as described above.

An exemplary procedure for following a therapeutic approach to acute renal failure is described below. Acute renal failure as employed herein is defined as involving a prephase polyuria associated with rising creatinine and urea values in the patient plasma, urea concentration of less than 300 mg/dl in the urine, urine volume of less than 500 ml/24 hours, and urine pH of less than about 6. Additional aspects which can be observed are low inorganic phosphate and titratable acid levels in the urine.

Upon having recognised incipient acute renal failure, immediately infuse an infusible solution of sodium bicarbonate, conveniently a 1 molar (8.4%) solution with the aid of a central venous catheter. An estimate of the total sodium bicarbonate required can be made on the basis of the degree of serum base deficit determined (−BE) according to the formula:

$$0.3 \times \Delta BE \times body\ weight = ml\ 1\ molar\ NaHCO_3$$

In the light of clinical experimentation and experience to date, best results are obtained when an amount of sodium bicarbonate is administered which leads to a slight metabolic alkalosis reflecting a base excess, for example BE+5 m Eq/l. An example of a determination of dosage with a measured BE=−10 mEq/l and a desired BE=+5 mEq/l is as follows:

$$\Delta BE = 15\ mEq/l$$

In above equation:

$$0.3 \times 15 \times 70 = 350\ ml\ (1\ molar\ NaHCO_3)$$

Contrary to earlier indications of the dangers of sodium bicarbonate therapy, probably based on general lack of recognition of the secondary effects described, these dangers are few and are relative in that corrective measures are available for most conditions which are likely to arise. For example hypersodemia and hypocalcemia can be prevented and pulmonary insufficiency which might arise can be supported by patient ventilation. On the other hand, there are some conditions where success in reversing acute renal failure by administration of sodium bicarbonate should not be expected, such as irreversible shock associated with circulatory insufficiency, toxic acute renal failure and toxic renal failure due to poisoning. In these situations blood dialysis is necessary.

Of high importance is the preventive or prophylactic approach to acute renal failure which can frequently be prevented if intravenous administration of sodium bicarbonate is effected soon after onset of renal failure is recognised. Furthermore, however, it has been found that acute renal failure can be prevented by prophylactic administration of quantities of sodium bicarbonate, for example preliminary to severe medical and surgical treatment, or immediately following severe intoxications. Exemplary are kidney transplant recipients and donors, preoperative conditioning of patients with varying degrees of renal insufficiency, such as may be related to diabetis, age and pregnancy. As already explained in connection with establishing doses to be administered, it is most preferable to establish a so-called "plasma base excess". A consideration related to this preference is the fact that observations made in reversing of acute renal failure, namely to the point where polyuria sets in, have reflected a preliminary almost simultaneous increase in fresh patient urine pH value to about neutral or alkaline suggesting passage of excess bicarbonate.

The surprising success of alkali-induced polyuria, even in cases where the entire conventional therapeutic measures had been employed without success, has led to consideration of possible methods of treatment additional to those of acute renal failure. Particularly, consideration has been given to whether or not the findings in the reversal and prevention of acute renal failure, involving intravenous administration, which is not without danger of complication in some circumstances, might also find application in the treatment of subjects suffering from altered renal function or even renal insufficiency of varying degrees.

It is recognised that patients suffering from chronic renal disease characteristically display, irrespective of the type of such disease, an increase in retention products, such as urea, creatinine and uric acid, which are normally discharged through the kidneys. When these substances attain a certain level, a clinical picture of uremia is obtained, which is a threat to life and can ultimately only be treated with the aid of the artificial kidney. Due to the increased concentration of hydrogen ions, which accompanies the increase of these substances which should be eliminated by urine entrainment, hyperacidity or, metabolic acidosis results. Hence, patients with advanced renal insufficiency display a marked hyperacidity, which has also been recognised to at least be a partial cause of various other states of ill health, such as disorders in the bone metabolism and mineral metabolism.

From the experience in treating, preventing and conditioning against acute renal failure, the possibilities of advantage of neutralising at least in part metabolic acidosis as described above have been further examined. In this respect, it should be noted that administration of substances having an alkaline effect in an effort to neutralise metabolic acidosis has been attempted. For example, the intravenous injection of sodium bicarbonate solutions is described by K.E. Thoma in "Med. Klin." $f(1976)$ 124-127. Furthermore, the oral administration of a hexa potassium-hexasodium-penta-hydrate-complex or a potassium-free hexacalcium-hexasodium-heptacitrate-hydrate-complex is described in "Diagnostik" 10 (1977) 569-572. However, intravenous injection would not be an acceptable procedure for therapy of chronic renal insufficiency and the oral administration described leaves much to be desired in that larger amounts of these complexes need to be taken with large amounts of liquid, which frequently causes flatulence, nausea and vomiting. Moreover, these complexes are in part eliminated undigested. It is accordingly difficult to achieve sodium bicarbonate levels produced by metabolism of the complexes required for correcting metabolic acidosis.

Also generally known for many years is the use of sodium bicarbonate for treating acid indigestion, again a procedure creating flatulence, nausea and possibly vomiting. Such administration basically involves treatment of hyperacidity in the stomach and would generally involve a single dose. Attempt which might be made to employ sodium bicarbonate to neutralise at least in part metabolic acidosis can only have limited success in that relatively large amounts would be required to raise plasma sodium bicarbonate content sufficiently to exercise an adequate corrective effect on metabolic acidosis. Although such a procedure should not be eliminated altogether and is not excluded as a potential means for correcting at least in part metabolic acidosis in some circumstances, it should be noted here that the amounts of sodium bicarbonate required would lead to development of substantial amounts of sodium chloride in the stomach, an increased discharge of hydrochloric acid by the stomach and hence yet further development of amounts of sodium chloride. Patients suffering from renal insufficiency are inclined to suffer from hypertension and increased amounts of sodium chloride, which has a hypertensive effect, is accordingly of disadvantage particularly in that hypertension is of high danger to the patient's life expectancy.

The overall views held today in the medical profession is that attempt to neutralise metabolic acidosis in chronic renal failure, leads to disadvantages which outweigh any advantages which may be achieved. A variety of reasons are reported, and as several times mentioned, there exists an overall prejudice against administration of sodium bicarbonate. One example additional to hypertension is that increased sodium in the body leads to edema.

It is an object of this invention, and one quite distinct from the findings related to acute renal failure discussed above, to establish an acceptable procedure for raising plasma bicarbonate levels without need to resort to intravenous administration (such as would be necessary in acute patient conditions) and avoiding complications of the nature discussed above. Essentially, it has been found that increase of plasma bicarbonate levels is of extreme benefit in spite of the prejudice against such approach. Indeed, the finding of an acceptable procedure for increasing plasma bicarbonate levels has revealed extraordinary utility in the most varying types of ailments, including practically any form of abnormal body fluid retention. For example, elderly patients (who might also be suffering from incomplete renal function) exhibiting such conditions to dropsy, peripheral edemas, varicose veins and like disturbances have in many cases responded extraordinarily well to treatment with the novel pharmaceutical preparation of the present invention. Particularly, however, bearing also in mind that the present studies and the pharmaceutical preparation which has emanated therefrom, is related to treatment of abnormal distribution and retention of body fluids as a result of altered renal function, it is this aspect of utility which will be discussed in greater detail below.

It has been found that in a fashion somewhat similar to that described above in relation to acute renal failure, a therapeutic procedure involving increase of plasma bicarbonate levels to correct at least in part metabolic acidosis existent in patients suffering from renal insufficiency has extraordinarily and surprisingly beneficial effects. Thus, it has been found that substantial correction of metabolic acidosis in such patients can in a large number of cases enormously increase urine production and similarly enormously increase clearance of retention products. Effects are in some cases so marked that patients who would in due course need to be subjected to blood dialysis can either not need to be subjected to this form of treatment at all, or such can be considerably postponed. Apparently, the increase in plasma bicarbonate level and consequent correction of metabolic acidosis induces an alkalotic volume contraction of the nature discussed in the initial stages of this disclosure. This driving force is believed to enable remaining functioning sections of the kidney to increase in function, i.e. urine output, sometimes to an extent sufficient for a patient, even dialysis patients to remain in an adequate metabolic state of water and acid-base balance. Moreover, the state of bicarbonate-induced alkalotic volume contraction may have the effect of lowering elevated blood pressure, which is a finding of considerable surprise since all indications to date are that sodium bicarbonate administration leads to the reverse result.

The procedure for treatment of the above nature involves increasing plasma bicarbonate levels by oral administration of a pharmaceutically acceptable alkaline acting substance. More particularly, although other alkaline acting substances might find application in this method of the present invention, the alkaline acting substance would be adapted to release sodium and bicarbonate ions. Release of bicarbonate ions and availability thereof to restore depleted extracellular reserves in metabolic acidosis is at this time considered to be of importance. In a fashion similar to that described in relation to acute renal failure it is preferable to administer sufficient alkaline acting substance to achieve a plasma base excess in the patient, which can for example very easily be monitored by determining fresh patient urine pH value. Thus, for example, patient urine pH values in the neutral to alkaline region provides a convenient means to confirm alkalotic patient condition.

The means to establish the high alkaline level by oral administration necessary to achieve increased plasma bicarbonate level is achieved in a fashion considered to be of high importance and value in that it involves the entirely different therapeutic approach described above and also a particular pharmaceutical form adapted to be released in the intestinal tract so that the alkaline acting substance is easily resorbed without the variety of complications such as mentioned in conjunction with administration of alkaline acting substances employed in the past. More particularly, and in accordance with the invention, the alkaline acting substance, such as one capable of releasing sodium and bicarbonate ions, is formed into a pharmaceutical oral dosage form adapted to release the alkaline acting substance in the alkaline environment of the small intestine, notably at resorption sites. Very considerably higher rates of resorption as compared to resorption which may take place following on a release of the alkaline acting substance in the acid environment of the stomach can be achieved. Accordingly, correspondingly lower dosages to achieve the desired elevated plasma bicarbonate levels can be employed.

Exemplary unit dosage forms found to be convenient comprise from about 500 to about 1500 mg of alkaline acting substance, such as sodium bicarbonate. Unit dosage forms may be tablets, capsules or dragees enclosed by an acid-resistant (gastric-juice resistant) alkali-decomposable enclosure. In that the enclosure needs to be decomposable in the only moderately alkaline environment of the small intestine and in that the substance enclosed is also alkaline, or would be alkaline if liquid were to penetrate the coating prematurely, the preparation of the oral dosage forms of the invention is not entirely without difficulty. However satisfactory results can be achieved with tablets, dragees and granulates coated with acrylic resins resistant to gastric juice, such as marketed by Röhm Pharma under the trademark "EUDRAGIT S". Similarly capsules comprising the alkali acting substance may be rendered resistant to gastric juice by treatment with a mixture of hydroxypropyl methyl cellulose phthalate and dibutyl phthalate. A variety of other coatings suitable for the indicated purpose may of course also be employed.

It is appropriate to mention at this juncture, and particularly in relation to dosages to be administered in accordance with treatment procedures and in accordance with the present invention, that correction of metabolic acidosis insofar as such may have been attempted in the past, has lacked proper recognition of the necessary plasma bicarbonate level, the need for maintenance of such level, and at least in the case of treatment of metabolic acidosis conditions (of even slight degree) which are existent in renal insufficiency circumstances, means whereby sufficient alkaline acting substance such as a substance capable of releasing a cation such as sodium and bicarbonate ions, has not been available.

Clinical evaluations have reflected that best results are achieved in the treatment of abnormal body fluid distribution such as result from altered renal function when the amount of alkaline acting substance administered is sufficient to create (and maintain) a moderate degree of metabolic alkalosis. Thus, as may be determined by blood gas analysis, bicarbonate concentrations in plasma should preferably lie above 24 mEq/l and most preferably above 26 mEq/l, which corresponds to about a 4 to 5 mEq/l base excess value. Dosages which need to be applied to achieve values such as described above are of course dependent on the particular condition being treated. However, in general, it has been found that dosages ranging between 0.5 and 10 g/24 hours are adequate to establish preferred fresh patient urine pH value of above 6.5 and most preferably neutral to alkaline at a pH value between 6.8 and 8. Indeed, most preferably, in view of indications reflected in the therapy of renal insufficiency, adequate renal function is regularly only established while fresh patient urine pH values are in the neutral to alkaline range.

It has already been indicated above that increased urine volume established by increased plasma bicarbonate levels leads to an associated increased elimination of retention products. Another surprising factor is that various conditions of edema, have been observed to be aleviated. This is of particular note in that increased sodium levels, such as would be expected from administration of sodium bicarbonate, have in the past been considered to be a cause of edema.

There has been mention above of treatment of a variety of ailments reflected by abnormal distribution and retention of body fluids, for example as may occur in old age, pregnancy and dietary indiscretion. The oral preparation of the present invention, it should be noted can advantageously comprise additional active agents. For example, the oral preparations of the present invention may comprise a nutrient such as glucose, phosphates, and amino acids, a diuretic, urea, digestive acids, and enzymes. Furthermore, for purposes of correcting possible states of hypocalcemia or potassemia an amount of a calcium product, such as calcium gluconate or an amount of a potassium compound, such as potassium chloride, potassium bicarbonate and potassium citrate, may be included in the oral preparations of the invention.

It has been observed above that the treatment procedures of the present invention also comprise prophylactic approaches. One prophylactic approach worthy of mention is prevention of the formation of kidney stones. Such prophylactic action may be encouraged by inclusion in oral preparations of substances such as alkali or alkali earth metal citrates, or inclusion of urea itself. Thus, where increased urine volume may be encouraged by creating a state of alkalotic volume contraction, presence of increased amounts of citrate or urea in the urine volume can decrease tendencies of kidney stone formation. In like manner, presence of increased amounts of citrate or urea in increased urine volumes can regularly be successfully employed to assist in the elimination of kidney stone fines and kidney stones. For purposes of maintaining a general state of well-being, particularly in elderly patients, trace elements today recognised to contribute to such may be included in oral preparations. Already mentioned is that elderly people commonly suffer from altered renal function.

A major consideration of the present invention is associated with the finding that effective therapeutical treatment of altered renal function can be achieved by oral administration of an alkaline acting substance, in particular one capable of liberating bicarbonate ions to replace bicarbonate reserves normally present in extracellular fluids, and more particularly sodium bicarbonate. Some consideration has been applied to methods which might be attempted to circumvent the concepts of this invention, for example by associating enteral administrations of pharmaceuticals of recognised therapeutic value with sodium bicarbonate. For this reason also, it is here explicitly stated that the present invention recognises and claims hereinafter oral preparations, particularly such as may be employed in the therapy of a large variety of diseases and ailments which can be as a result of partial or temporarily altered renal function, which comprises alkaline acting substance such as sodium and bicarbonate ion liberating substances, in association with further pharmaceuticals.

Oral preparations of the present invention are highly effective in increasing urine volume when administered at correct minimum dosage levels as herein described and have been found to exercise extraordinarily beneficial effects in the therapy of a multitude of body fluid distribution and fluid retention disorders.

What we claim is:

1. A method of treating a subject suffering from abnormal distribution and retention of body fluids and retention products which is as a result of altered renal function, which comprises orally administering to a subject in need of such treatment, a therapeutically effective amount of an oral dosage form of a pharmaceutically acceptable alkaline acting substance adapted to release sodium and bicarbonate ions in the small intestine of the subject and being capable of increasing patient plasma bicarbonate level to a value in excess of that prior to treatment, the therapeutically effective amount being sufficient to substantially correct metabolic acidosis and increase urine production and clearance of retention products.

2. A method according to claim 1, in which the therapeutically effective amount of the alkaline acting substance is estimated on the basis of the body weight of the subject and a determined plasma base deficit.

3. A method according to claim 1, in which the therapeutically effective amount of the alkaline acting substance is sufficient to establish a plasma base excess in the subject.

4. A method according to claim 1, in which the therapeutically effective amount of the alkaline acting substance is at least sufficient to lead to a detectable increase in fresh patient urine pH value over that prior to treatment.

5. A method according to claim 1, in which the patient plasma bicarbonate level is maintained at said increased value by intermittent administration of the alkaline acting substance.

6. A method according to claim 4, in which the fresh patient urine pH value is increased to said increased value each time the fresh patient urine pH value falls below said increased value, by further administration of an amount of the alkaline acting substance.

7. A method according to claim 1, in which the maintenance of said increased patient plasma bicarbonate level is determined by observing a maintained increased fresh patient urine pH value.

8. A method according to claim 1, in which the amount of alkaline acting substance administered to maintain said increased patient plasma bicarbonate level is sufficient to maintain fresh patient urine pH value in excess of 6.5.

9. A method according to claim 8, in which the amount of alkaline acting substance administered is sufficient to maintain fresh patient urine pH value between 6.8 and 8.

10. A method according to claim 1, in which the alkaline acting substance is sodium bicarbonate.

11. An oral dosage form of an alkaline active substance capable of increasing plasma bicarbonate level to a value in excess of that prior to treatment, for use in the method of claim 1.

12. An oral dosage form according to claim 11, comprising sodium bicarbonate enclosed within an acid-resistant alkali-decomposable enclosure.

13. An oral dosage form according to claim 12, in which the acid-resistant alkali-decomposable enclosure comprises a gastric juice resistant acrylic resin.

14. An oral dosage form according to claim 12, in which the acid-resistant alkali-decomposable enclosure is a capsule enclosure rendered resistant to gastric juice with the aid of a mixture of hydroxypropyl methyl cellulose phthalate and dibutyl phthalate.

15. An oral dosage form according to claim 11, in which the alkaline acting substance is associated with additional active agents, such as may be employed in the therapy of diseases and ailments which can be as a result of partial or temporarily altered renal function.

16. An oral dosage form according to claim 15, in which the additional active agents are selected from substances suitable for the prophylaxis and therapy of kidney stones, selected from the group consisting of an alkali metal or alkaline earth metal salt of citric acid, or urea.

17. An oral dosage form according to claim 15, in which the additional active agent is a calcium compound suitable for supplementing calcium in a subject.

18. An oral dosage form according to claim 17, in which the calcium compound is calcium gluconate.

19. An oral dosage form according to claim 15, in which the additional active agent is a potassium compound suitable for supplementing potassium in a subject.

20. An oral dosage form according to claim 19, in which the potassium compound is one or more of potassium chloride, potassium bicarbonate, and potassium citrate.

21. An oral dosage form according to claim 11, in unit dosage form, comprising from about 500 to about 1500 mg of sodium bicarbonate enclosed within an acid-resistant alkali-decomposable enclosure enabling release of sodium and bicarbonate ions in the small intestine of a subject.

22. An oral dosage form according to claim 15, in which trace elements recognised to contribute to the general well-being of patients are comprised in the oral dosage form.

* * * * *